(12) United States Patent
Brungart

(10) Patent No.: US 9,807,519 B2
(45) Date of Patent: Oct. 31, 2017

(54) METHOD AND APPARATUS FOR ANALYZING AND VISUALIZING THE PERFORMANCE OF FREQUENCY LOWERING HEARING AIDS

(71) Applicant: Douglas S. Brungart, Rockville, MD (US)

(72) Inventor: Douglas S. Brungart, Rockville, MD (US)

(73) Assignee: The United States of America as Represented by the Secretary of Defense, Washington, DC (US)

( * ) Notice: Subject to any disclaimer, the term of this patent is extended or adjusted under 35 U.S.C. 154(b) by 54 days.

(21) Appl. No.: 14/456,252

(22) Filed: Aug. 11, 2014

(65) Prior Publication Data

US 2015/0078561 A1    Mar. 19, 2015

Related U.S. Application Data

(60) Provisional application No. 61/864,068, filed on Aug. 9, 2013.

(51) Int. Cl.
*H04R 25/00* (2006.01)
*H04R 29/00* (2006.01)
(Continued)

(52) U.S. Cl.
CPC .......... *H04R 25/30* (2013.01); *H04R 29/008* (2013.01); *A61B 5/04845* (2013.01); *A61B 5/12* (2013.01);
(Continued)

(58) Field of Classification Search
CPC ...... H04R 25/30; H04R 25/40; A61B 5/7257; A61B 5/12
See application file for complete search history.

(56) References Cited

U.S. PATENT DOCUMENTS 4,809,708 A * 3/1989 Geisler ................ A61B 5/6817
600/552
5,325,436 A * 6/1994 Soli ........................ H04R 5/027
381/26

(Continued)

FOREIGN PATENT DOCUMENTS

CH    WO 2007107292 A2 * 9/2007 ............. H04R 25/70

OTHER PUBLICATIONS

Glista et al; Modified Approaches for frequency lowering devices, audiology online, Nov. 2009.*
(Continued)

*Primary Examiner* — Davetta W Goins
*Assistant Examiner* — Kuassi Ganmavo
(74) *Attorney, Agent, or Firm* — Diane P. Tso; Ning Yang; Albert M. Churilla

(57) ABSTRACT

A method of analyzing performance of frequency lowering hearing aids. The method includes generating a sequentially of noise signals and transmitting acoustical sounds from a sound output device in response to the sequence of noise signals. A sound input device records the acoustical sounds and saves as a first device data. The sound input device with a frequency lowering hearing aid records the acoustical sounds and save as a second device data. The second device data is compared to the first device data and, in response to the comparison, at least one function of the frequency lowering hearing aid is optionally adjusted.

17 Claims, 15 Drawing Sheets

(51) Int. Cl.
*A61B 5/0484* (2006.01)
*A61B 5/12* (2006.01)
*A61B 5/00* (2006.01)

(52) U.S. Cl.
CPC .............. *A61B 5/121* (2013.01); *A61B 5/6817* (2013.01); *A61B 5/7257* (2013.01); *H04R 25/353* (2013.01); *H04R 25/505* (2013.01); *H04R 29/004* (2013.01)

(56) References Cited

U.S. PATENT DOCUMENTS

| | | | | |
|---|---|---|---|---|
| 6,379,314 | B1* | 4/2002 | Horn | A61B 5/121 600/559 |
| 6,577,739 | B1 | 6/2003 | Hurtig et al. | |
| 6,792,114 | B1* | 9/2004 | Kates | H04R 25/305 381/60 |
| 7,248,711 | B2 | 7/2007 | Allegro et al. | |
| 8,135,139 | B2 | 3/2012 | Neher et al. | |
| 8,315,402 | B2 | 11/2012 | Zhang et al. | |
| 8,494,199 | B2 | 7/2013 | Kates | |
| 2003/0072464 | A1* | 4/2003 | Kates | G10H 1/125 381/312 |
| 2004/0057591 | A1* | 3/2004 | Beck | H04R 25/552 381/315 |
| 2004/0158431 | A1* | 8/2004 | Dittberner | H04R 25/30 702/183 |
| 2005/0123146 | A1* | 6/2005 | Voix | A61F 11/08 381/60 |
| 2006/0045282 | A1* | 3/2006 | Reber | A61B 5/12 381/60 |
| 2006/0188105 | A1* | 8/2006 | Baskerville | A61F 11/08 381/60 |
| 2009/0129619 | A1* | 5/2009 | Nordahn | H04R 25/70 381/328 |
| 2010/0104122 | A1* | 4/2010 | Waldmann | H04R 25/70 381/314 |
| 2010/0254554 | A1* | 10/2010 | Fusakawa | H04R 25/558 381/315 |
| 2011/0142272 | A1* | 6/2011 | Takagi | A61B 5/121 381/321 |
| 2012/0288108 | A1* | 11/2012 | Adachi | A61B 5/04845 381/60 |
| 2013/0121496 | A1* | 5/2013 | Boretzki | H04R 25/70 381/60 |
| 2013/0187924 | A1* | 7/2013 | Ogata | G06T 11/206 345/440 |
| 2014/0321657 | A1* | 10/2014 | Stirnemann | H04R 25/70 381/60 |

OTHER PUBLICATIONS

Xiao et al, Evaluation of frequency lowering algorithms for intelligibility of chinese speech in hearing aids users, 2009.*

Simpson, Frequency Lowering Devices for managing High Frequency Hearing Loss: A review, 2009.*

Parent, Comparison of performance with Frequency Transposition Hearing Aids and Conventional Hearing Aids, JAAA, 1997.*

Hines, Comparing Hearing Aids Algorithm Performance using simulated performance intensity functions, DIT, 2011.*

G. Ramos et al., "Direct method with random optimization for loudspeaker equalization using IIR parametric filters," Acoustics, Speech, and Signal Processing, Proceedings. (ICASSP '04). IEEE International Conference, vol. 4 (2004) iv-97-iv-100.

University of Illinois at Urbana-Champaign, "Center frequencies and high/low frequency limits for octave bands, ½- and ⅓-octave bands," Physics 406 Acoustical Physics of Music, Lab Handouts (Published before Jan. 24, 2013) Available at https://courses.physics.illinois.edu/phys406/lab_handouts/octave_bands.pdf (accessed Aug. 11, 2014), 3 pages total.

R. Bentler, "Frequency-lowering hearing aids: verification tools and research needs." The ASHA Leader. (Apr. 6, 2010) Available at http://www.asha.org/Publications/leader/2010/100406/Frequency-Lowering-Hearing-Aids.htm (accessed Aug. 11, 2014), 4 pages total.

J. A. Galster, et al., "Spectral IQ: audibly improving access to high-frequency sounds," Starkey Laboratories, Inc. White Paper (2011) Available at https://starkeypro.com/pdfs/technical-papers/Spectral_iQ_Technical_Paper.pdf (accessed Aug. 11, 2014), 8 pages total.

F. Kuk et al., "Linear frequency transposition: extending the audibility of high-frequency information," The Hearing Review. (Oct. 8, 2006) Available at http://www.hearingreview.com/2006/10/linear-frequency-transposition-extending-the-audibility-ofhigh-frequency-information/ (accessed Aug. 11, 2014), 7 pages total.

Phonak, "SoundRecover—a breakthrough in enhancing intelligbility," Audiology Online (Jun. 6, 2008) Available at http://www.audiologyonline.com/releases/soundrecover-breakthrough-in-enhancing-intelligibility-3719 (accessed Aug. 11, 2014), 6 pages total.

D. Glista et al., "Evaluation of nonlinear frequency compression: Clinical Outcomes," Int'l J Audiology. vol. 48 (2009) 632-644.

R. V. Shannon et al., "Speech recognition with primarily temporal cues," Science. vol. 270 (1995) 303-304.

M. Valente et al., "Guildeines for the audiologic management of adult hearing impairment," Auiod Today. vol. 18 (2006) 32-37.

* cited by examiner

METHOD AND APPARATUS FOR ANALYZING AND VISUALIZING THE PERFORMANCE OF FREQUENCY LOWERING HEARING AIDS

Pursuant to 37 C.F.R. §1.78(a)(4), this application claims the benefit of and priority to prior filed, Provisional Application No. 61/864,068, filed 9 Aug. 2013, the disclosure of which is expressly incorporated herein by reference, in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to hearing aids and, more particularly, to analyzing the performance of hearing aids.

BACKGROUND OF THE INVENTION

In the early days of hearing aids, there was no feasible way to acoustically measure the amount of gain being provided by a specific hearing aid at the time the hearing aid was being dispensed in a clinic. Accordingly, audiologists had to rely on the gain settings reported in the manufacturer's specifications when setting the gain of these devices to match a prescribed gain for a given patient. However, audiologists soon realized that there could be a substantial variation between the amount of gain in the manufacturer's specifications and an actual gain provided by the device. These differences were attributed, at least in part, to variability in the manufacturing process and differences in the acoustics and physical shape of the given patent's ear canals.

By the mid 1970's, tabletop acoustic hearing aid verification systems began to appear on the market. These conventional systems used electronic measurement systems to make real-time measurements of gain as a function of input sound level and frequency for a hearing aid placed in a small sound chamber with an acoustic coupler, as defined by ANSI S3.22 (Specification of hearing aid characteristics). While these conventional systems allowed audiologists to verify, and at least partially, and correct for gain variations due to manufacturing differences, audiologists could not account for variations in performance related to differences in the anatomy of the patient's ear canals.

At about the mid 1980's, real ear measurement ("REM") hearing aid verification systems began to appear on the market. The REM system was based on the use of probe microphones with tubes that were inserted under the hearing aids. The probe microphones were used to make acoustic measurements of the signal reaching the eardrums of a hearing impaired listener from a remote loudspeaker location in the free field, in accordance with ANSI S3.42 (Testing hearing aids with a broadband noise signal). These REM systems have been conventionally viewed as a preferred method of performing acoustic verification of hearing aids on hearing impaired patients.

While the REM system continues to improve, there remains deficiencies in that the conventional REM system cannot suitably verify the performance of newer generation of hearing aids that incorporate non-linear processing algorithms that shift the frequency composition of an acoustic signal in real time. For example, the newest generation of hearing aids incorporates non-linear, frequency lowering techniques that shift or compress the high-frequency components of sound (that would otherwise be inaudible for listeners having high-frequency hearing loss) down into a lower frequency range where the signal may be audible for these listeners. However, a serious impediment to the proper implementation of the technology is that current tabletop and real-ear acoustic verification systems for hearing aids do not provide a convenient way to evaluate or visualize the effect frequency lowering has on the signal produced by a hearing aid. Frequency lowering algorithms are now implemented on a significant proportion of the hearing aids dispensed in the US; however, there is presently no system that addresses the issue of acoustic verification in frequency shifting hearing instruments. This poses a significant problem for hearing aid dispensers in the US and world-wide. Since REM is considered the current standard practice for hearing aid fittings, a system or apparatus configured to address this deficiency would fill an important niche for the more than 13,000 Audiologists currently practicing in the U.S. and the many more hearing professionals and hearing aid dispensers practicing worldwide.

There remains a need for a simple, efficient, and intuitive method by which hearing professionals (e.g., clinicians, audiologists, and technicians) can assess an operational state of a hearing device (including, hearing aids) incorporating non-linear frequency shifting algorithms.

SUMMARY OF THE INVENTION

The present invention overcomes the foregoing problems and other shortcomings, drawbacks, and challenges of simply, efficiently, and intuitively analyzing the operational state of frequency lowering hearing aids. While the invention will be described in connection with certain embodiments, it will be understood that the invention is not limited to these embodiments. To the contrary, this invention includes all alternatives, modifications, and equivalents as may be included within the spirit and scope of the present invention.

In accordance with one embodiment of the present invention, a method of analyzing performance of frequency lowering hearing aids includes generating a sequentially of noise signals and transmitting acoustical sounds from a sound output device in response to the sequence of noise signals. A sound input device records the acoustical sounds and saves as a first device data. The sound input device with a frequency lowering hearing aid records the acoustical sounds and save as a second device data. The second device data is compared to the first device data and, in response to the comparison, at least one function of the frequency lowering hearing aid is optionally adjusted.

In accordance with another embodiment of the present invention, a method of visualizing a change in at least one character of the first and second device data includes plotting a value of the at least one character of the first device data and extending an arrow from the value of the at least one character of the first data to a value of the corresponding, at least one character of the second device data.

Yet another embodiment of the present invention is directed to a method of analyzing performance of frequency lowering hearing aids, which includes generating a sequentially of noise signals and transmitting acoustical sounds from a sound output device in response to the sequence of noise signals. A sound input device records the acoustical sounds and saves as a first device data. The sound input device with a frequency lowering hearing aid records the acoustical sounds and save as a second device data. At least one character of the second device data is compared to at least one character of the first device data and, based on the comparison, at least one function of the frequency lowering hearing aid is optionally adjusted.

The above and other objects and advantages of the present invention shall be made apparent from the accompanying drawings and the descriptions thereof.

BRIEF DESCRIPTION OF THE FIGURES

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Figure 1:
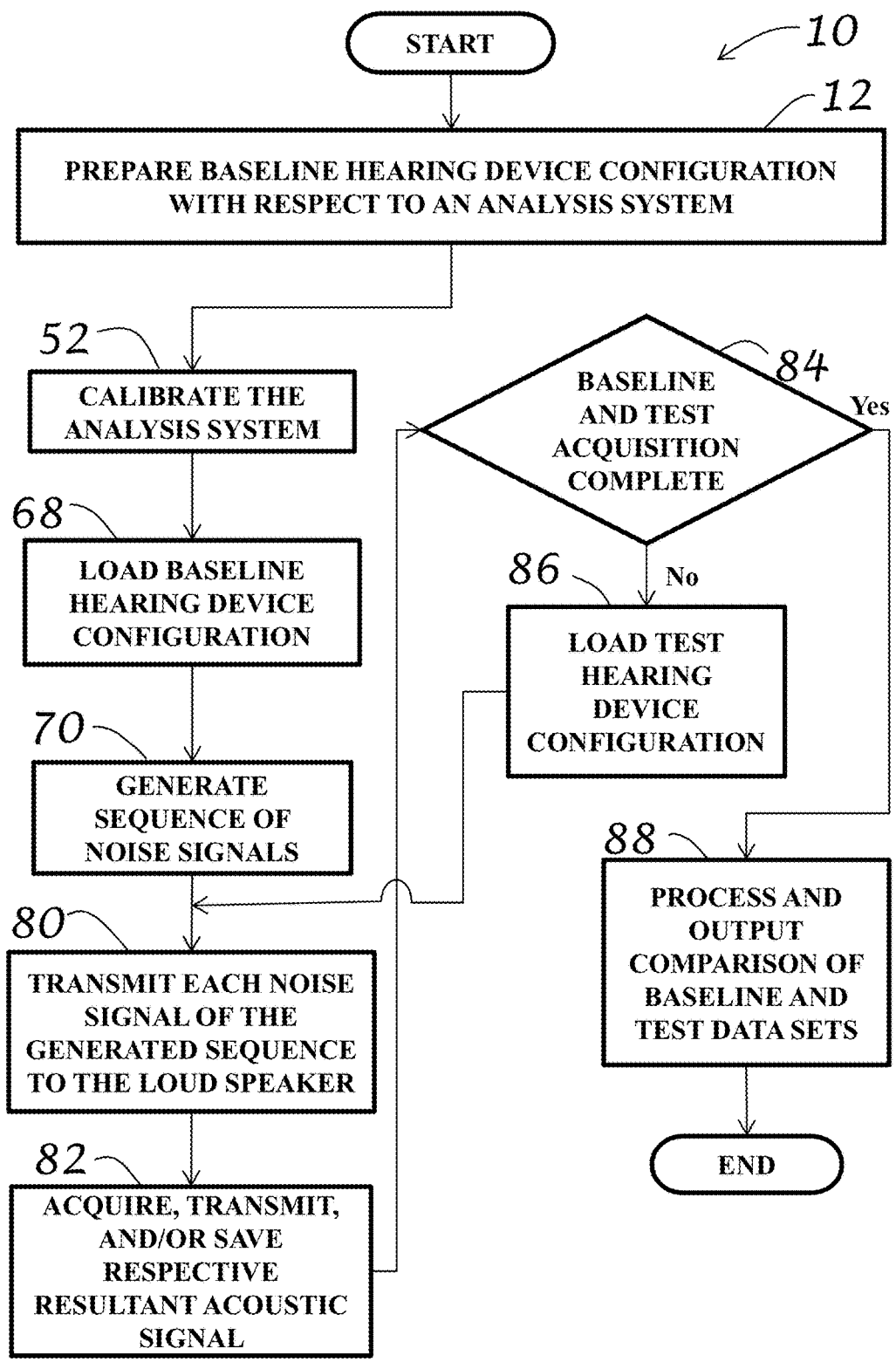
FIG. 1 is a flowchart illustrating a method of analyzing a performance of a frequency lowering hearing aid according to one embodiment of the present invention.
Figure 2:
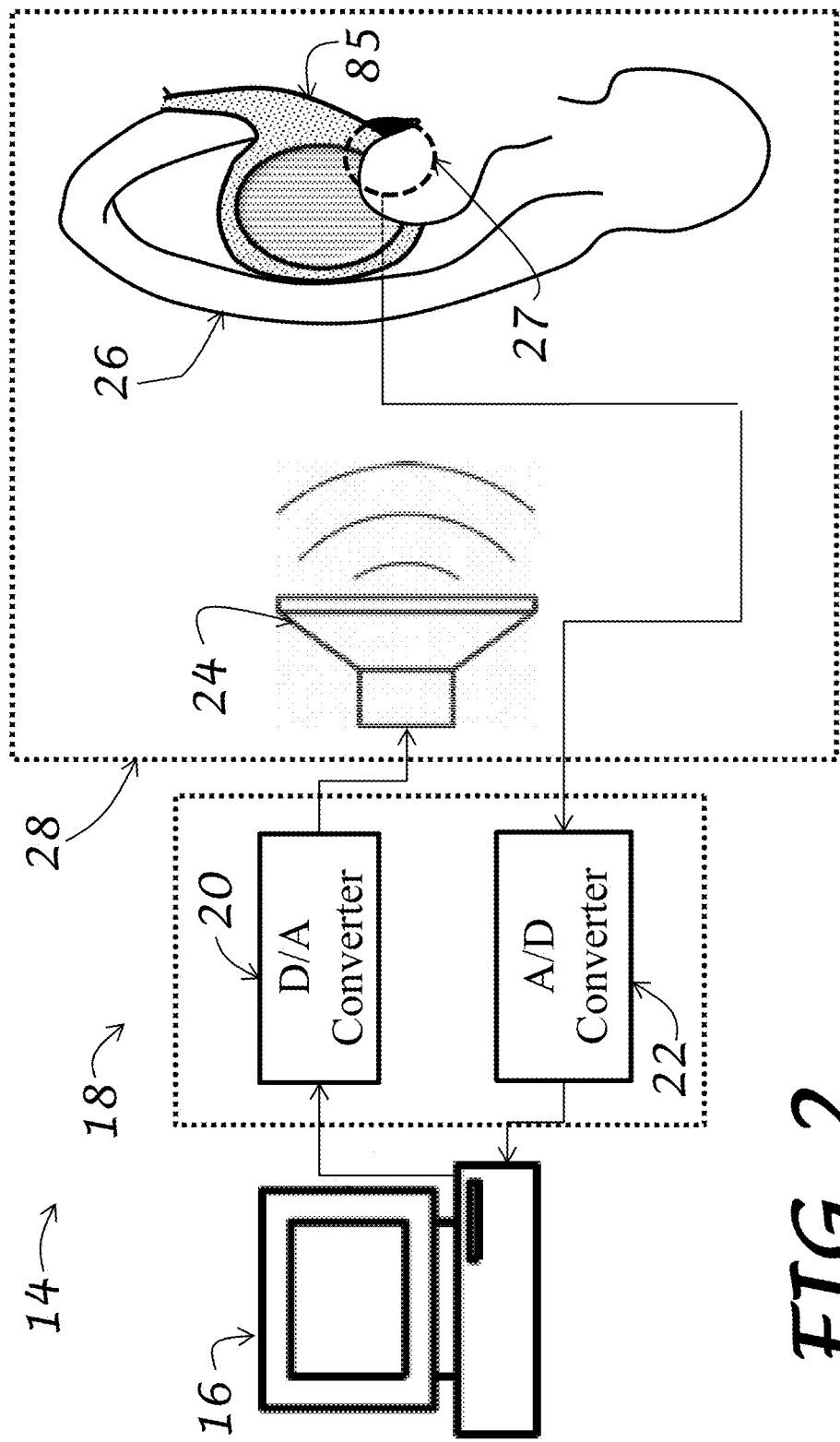
FIG. 2 is a schematic representation of one embodiment of an analysis system suitable for use in performing the method of FIG. 1.

Referring now to the figures, and in particular to FIG. 1, a flowchart 10 illustrating a method of analyzing a performance of a frequency lowering hearing device is described. At start, a baseline hearing device configuration is prepared (Block 12) with respect to an analysis system 14, which is shown in FIG. 2. More particularly, the analysis system 14 of FIG. 2 includes a computer 16 operably coupled to an audio interface 18 equipped with a digital-to-analog converter (illustrated as "D/A Converter" 20) and an analog-to-digital converter (illustrated as "A/D Converter" 22). An exemplary audio interface may include, for example, a Hammerfall DSP by RME (Haimhausen, Germany).

An output of the D/A Converter 20 is routed through a patch-panel (not shown) to a sound output device (illustrated herein as a loudspeaker 24, for example, a MeyerSound MX-4 by Meyer Sound Laboratories, Inc., Berkeley, Calif.) that is positioned within a sound-treated listening room 28. The sound output device 24 is directed toward either an acoustic manikin or a human listener (illustrated as an ear 26 of the manikin or human listener, as appropriate. An exemplary acoustic manikin may be a Knowles Acoustic Manikin for Auditory Research ("KEMAR"), which is equipped with at least one sound input device (such as an in-ear microphone 27) and at least one audio coupler, which are designed to simulate the acoustic properties of the external ear of a human listener. The human listener may have the microphone 27 placed in at least one ear, as is customary in using conventional REM acoustic verification devices. Outputs from the in-ear microphones 27 are routed back to the computer 16 via the A/D Converter 22.

Figure 3:
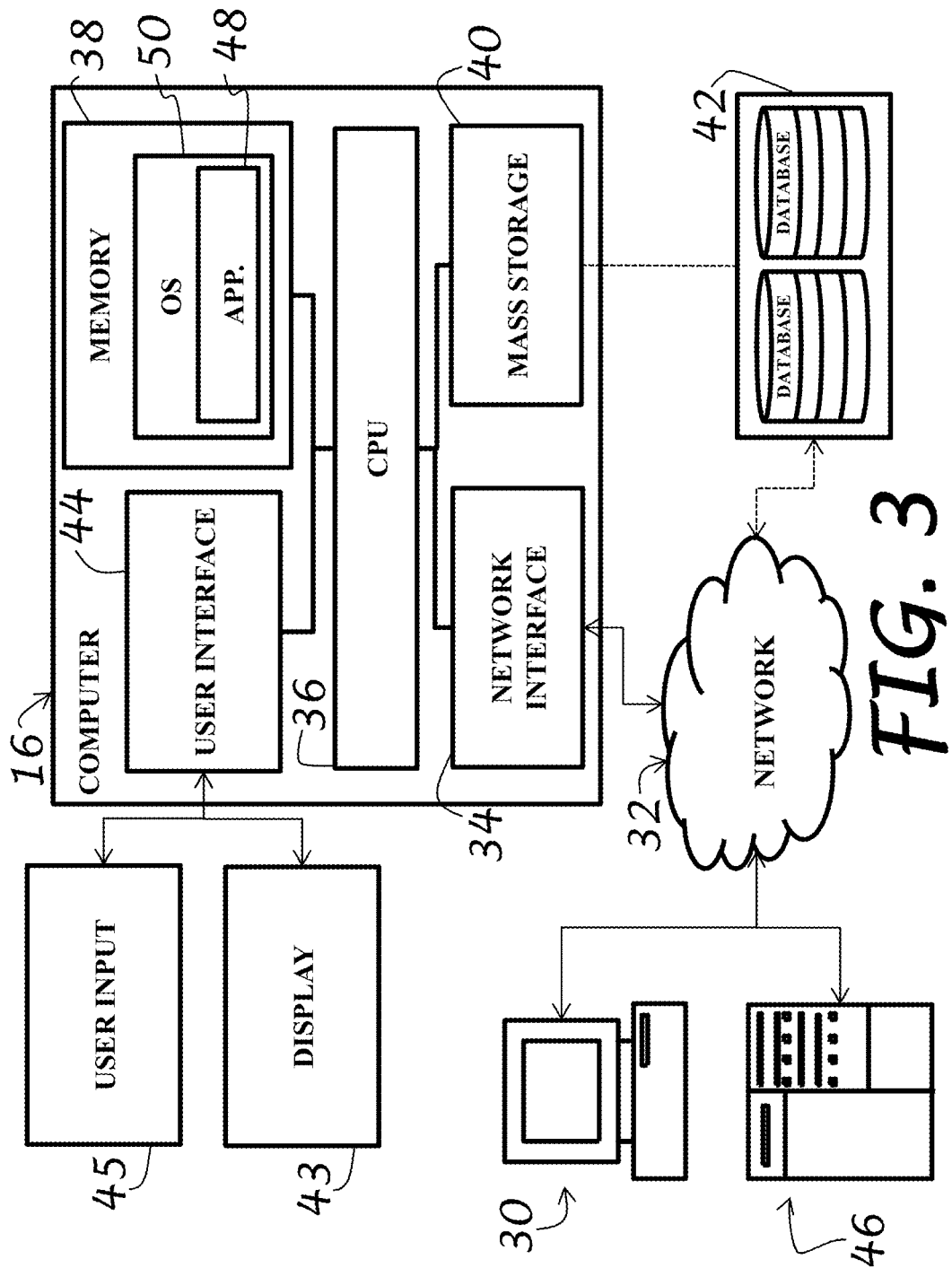
FIG. 3 is a schematic representation of a computer for use in the system of FIG. 2 and in employing the method of FIG. 1 according to an embodiment of the present invention.

The computer 16, as shown in greater detail in FIG. 3, may be considered to represent any type of computer, computer system, computing system, server, disk array, or programmable device, such as multi-user computers, single-user computers, handheld devices, networked devices, embedded devices, or existing stand-alone tabletop or REM acoustic hearing aid validation systems. The computer 16 may be implemented with one or more networked computers 30 using one or more networks 32, e.g., in a cluster or other distributed computing system through a network interface (illustrated as "NETWORK I/F" 34). The computer 16 will be referred to as "computer" for brevity's sake, although it should be appreciated that the term "computing system" may also include other suitable programmable electronic devices consistent with embodiments of the present invention.

The computer 16 typically includes at least one processing unit (illustrated as "CPU" 36) coupled to a memory 38 along with several different types of peripheral devices, e.g., a mass storage device 40 with one or more databases 42, the Network I/F 34, and input/output interface (illustrated as "USER INTERFACE" 44) operably coupled to a display 43 (such as a monitor) and a user input device 45 (such as a keyboard). The memory 38 may include dynamic random access memory ("DRAM"), static random access memory ("SRAM"), non-volatile random access memory ("NVRAM"), persistent memory, flash memory, at least one hard disk drive, and/or another digital storage medium. The mass storage device 40 is typically at least one hard disk drive and may be located externally to the computer 16, such as in a separate enclosure or in one or more networked computers 30, one or more networked storage devices (including, for example, a tape or optical drive), and/or one or more other networked devices 46 (including, for example, a server).

The CPU 36 may be, in various embodiments, a single-thread, multi-threaded, multi-core, and/or multi-element processing unit (not shown) as is well known in the art. In alternative embodiments, the computer 16 may include a plurality of processing units that may include single-thread processing units, multi-threaded processing units, multi-core processing units, multi-element processing units, and/or combinations thereof as is well known in the art. Similarly, the memory 38 may include one or more levels of data, instruction, and/or combination caches, with caches serving the individual processing unit or multiple processing units (not shown) as is well known in the art.

The memory 38 of the computer 16 may include one or more applications (illustrated as "APP." 48), or other software program, which are configured to execute in combination with the Operating System (illustrated as "OS" 50) and automatically perform tasks necessary for transmitting signals, acquiring signals, and analyzing signals, as necessary to analyze performance of a hearing device according to embodiments of the present invention with or without accessing further information or data from the database(s) 42 associated with the mass storage device 40.

Those skilled in the art will recognize that the environment illustrated in FIG. 3 is not intended to limit the present invention. Indeed, those skilled in the art will recognize that other alternative hardware and/or software environments may be used without departing from the scope of the invention.

Figure 4:
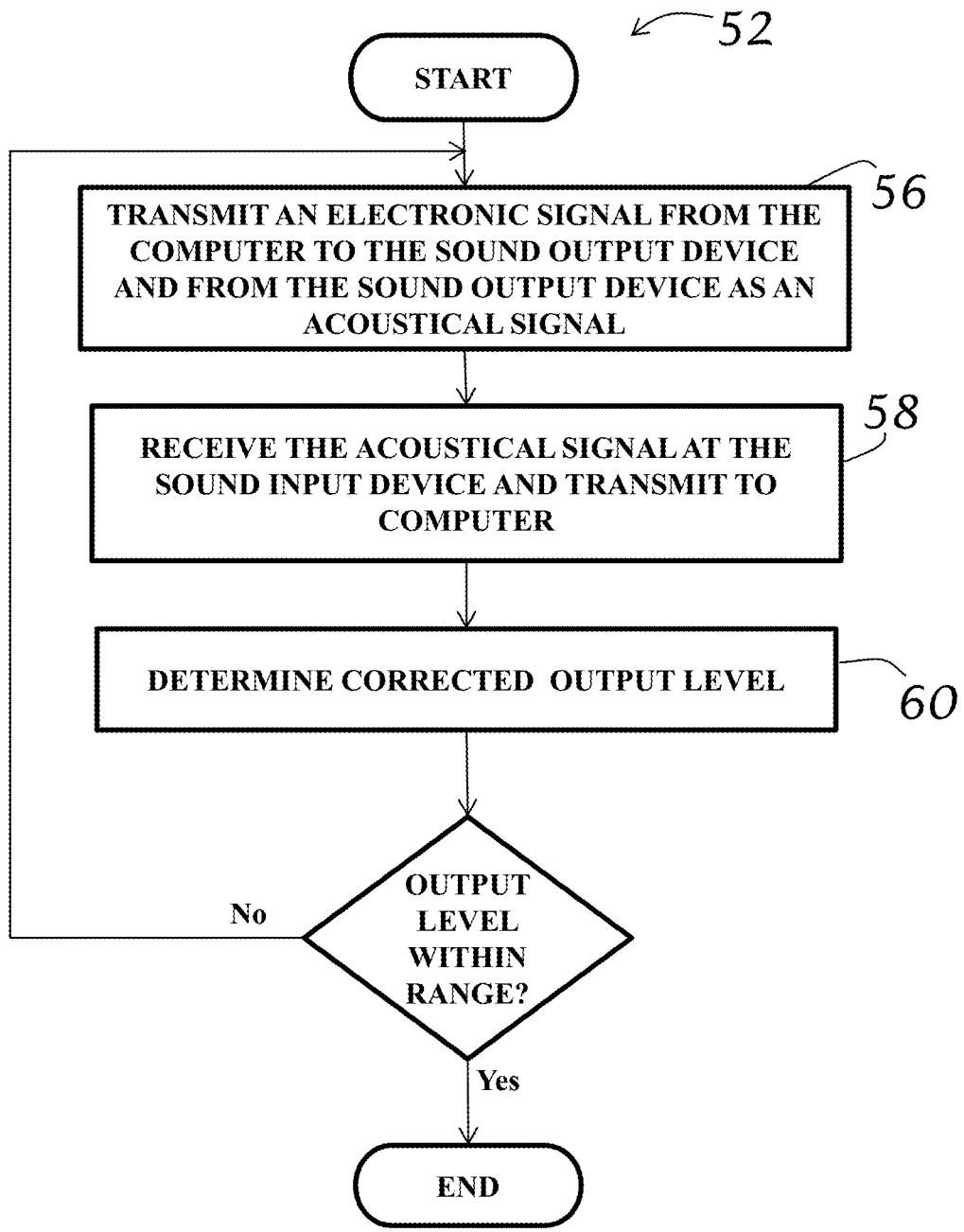
FIG. 4 is a flowchart illustrating a method of calibrating the analysis system of FIG. 2.

Referring again to FIGS. 1 and 2, and with the analysis system 14 prepared, the analysis system 14 may be calibrated (Block 52). Accordingly, and as shown in the flowchart 52 of FIG. 4, an electronic signal is generated by the computer 16 and transmitted via the D/A Converter 20 to the sound output device 24 and from the sound output device 24 as an acoustical signal (Block 56). The acoustical signal is received by the sound input device 27 and transmitted back to the computer 16 via the A/D Converter 22 (Block 58). Using the computer 16, a corrected output level may be determined, whereby a magnitude of that acoustical signal detected by the sound input device 27 is related to a magnitude of the electrical signal generated by the computer 16. Such determination may further include determination of an impulse response, $H_{spk}$ [n], which relates amplitude and phase spectra of the signal emitted by the sound output device 24 to amplitude and phase spectra of the signal received by the sound input device 27. Based on the determination, the acoustical signal as compared with the electrical signal is acceptable ("Yes" branch of Decision Block 60) and the method continues or, if unacceptable ("No" branch of Decision Block 60), the method returns for further evaluation.

Figure 5:
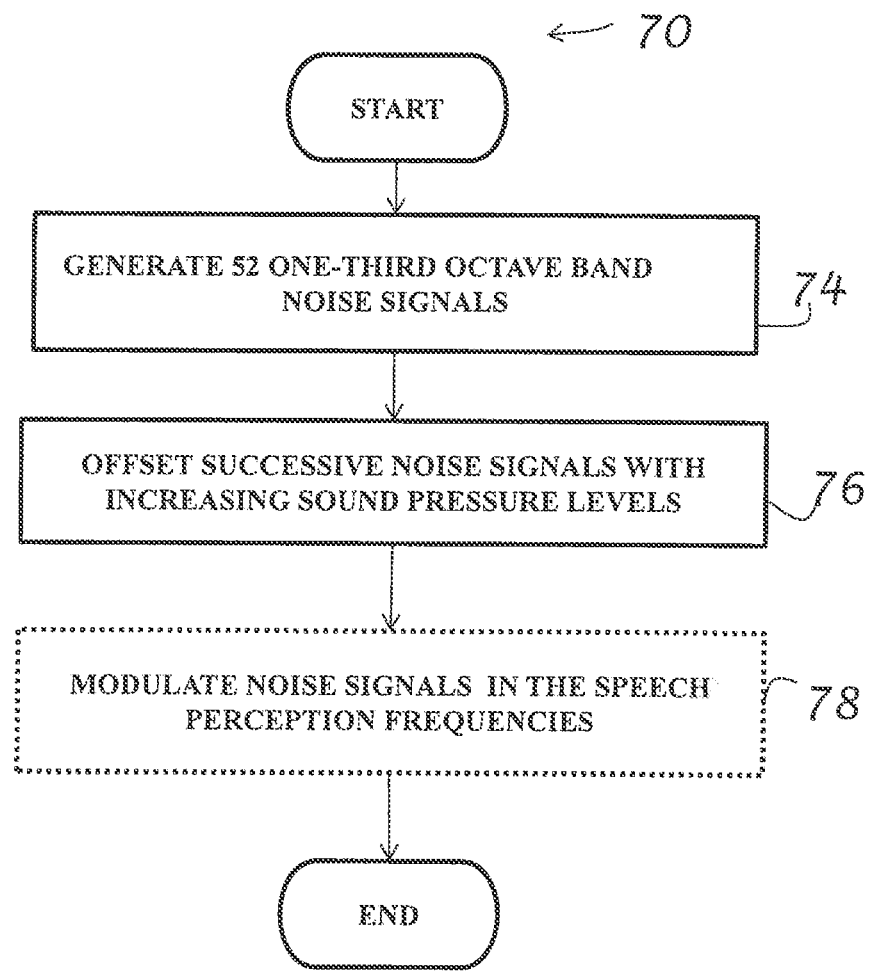
FIG. 5 is a flowchart illustrating a method of generating a sequence of noise signals, according to one embodiment of the present invention, and for use with the analysis system of FIG. 2.

With calibration complete (Block 52), and with reference again to FIGS. 1 and 2, a baseline acoustic configuration is loaded (Block 68). In that regard, the manikin 26 (or patient) having an open-ear condition (that is, the sound input device 27 without a hearing aid) is positioned within the listening room 28 and the computer 16 operated to generate a sequence of noise signals (Block 70). According to one embodiment of the method, which is shown in FIG. 5, the sequence of noise signals includes one-third octave-band wide noises having a time duration (for example, 2 sec) (Block 74). Each successive noise signal of the sequence may be one-twelfth octave higher in frequency than the immediately prior noise signal of the sequence. Resultantly, and according to some embodiments of the present invention, the sequence of noise signals may cover a range of frequencies (for example, from about 500 Hz to about 9514 Hz).

Besides varying frequency, successive bands within each frequency octave of the sequence of noise signals may be offset with increasing sound pressure levels ("SPL") (Block 76). For instance, a first band may be set to 50 dB SPL, a second band may be set to 60 dB SPL, a third band may be set to 70 dB SPL, and a fourth band may be set to 80 dB SPL (wherein all band sets are at a location at a center of the manikin's head). The successively next band, which would be the next frequency octave, may then return to the 50 dB SPL.

Additionally, and if desired, noise signals of the sequence may be optionally modulated with an envelope having random variations within speech perception frequencies (Block 78). That is, variations may be introduced in those frequencies ranging from about 4 Hz to about 16 Hz.

Returning to FIGS. 1 and 2, and with the sequence of noise signals generated (Block 70), each noise signal of the sequence may be transmitted to the sound output device 24 (FIG. 2), which generates the resultant acoustical signal (Block 80). The acoustical signal received by the sound input device 27 may be electrically transmitted to the computer 16, recorded, and/or saved as a baseline data set (Block 82).

After the baseline hearing device configuration data acquisition is complete ("No" branch of Decision Block 84), a test hearing device configuration may be loaded (Block 86). In other words, the analysis system 14 of FIG. 2 is prepared in a manner similar as described above but for the manikin 26 (or patient) having a hearing aid 85 with the hearing device 27 inserted into at least one ear 26. The process returns to Block 80 such that the sequence of noise signals is again transmitted. As described above, each noise signal of the sequence may be transmitted to the sound output device 24, which generates a resultant acoustical signal (Block 80). The acoustical signal received by the sound input device 27 through the hearing aid 85 and transmitted, recorded, and/or saved as a test data set by the computer 16 (Block 82).

After both the baseline and test hearing device configuration data acquisition is complete, ("Yes" branch of Decision Block 84), the process continues such that the acquired baseline and test data sets may be processed, compared, and, if desired, output in a visual display (Block 88).

Figure 6:
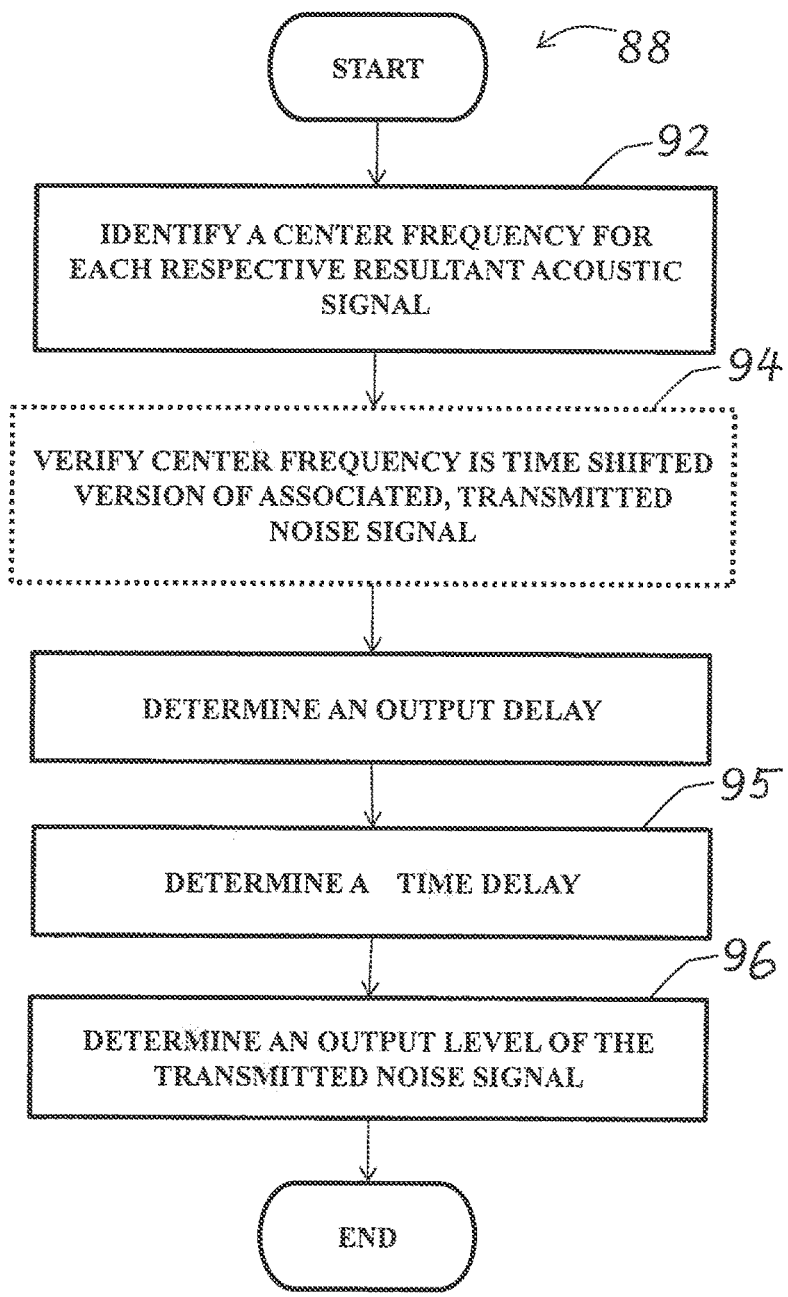
FIG. 6 is a flowchart illustrating a method, according to one embodiment of the present invention, of analyzing data acquired from the method of FIG. 1.

The processing method, according to one embodiment of the present invention, is described with reference to FIG. 6. Generally, at least one data point is identified for each acoustic signal of the baseline and test hearing data sets. According to the illustrated embodiment of the present invention, four data points (or characters) are identified and include: (1) a first data point being an estimated center frequency (Block 92); (2) a second data point being a coherence between transmitted and resultant signals (Block 94); (3) a third data point being a time delay (Block 95), and (4) a fourth data point being an output level of the transmitted noise signal (Block 96).

Determining the first data point, that is, the estimated center frequency of each acoustic signal of the baseline and test data sets (Block 92), according to one embodiment of the present invention, includes applying a Hanning window to each acoustic signal in a manner that is known to those of ordinary skill in the art of signal processing. For exemplary purposes, the Hanning window may be 670 ms long and positioned 1.7 sec after a time zero for each transmitted acoustical signal (that is, at an onset of noise signal emission from the sound output device). Offsetting the Hanning window by a set time may reduce or eliminate fluctuations due to non-linear compression circuitry of the sound input device and ensures that a steady state is established.

After windowing, the time domain of each acoustic signal of the baseline and test data sets is converted to a smooth magnitude, frequency domain spectrum, for example, by applying a Fast Fourier Transformation ("FFT"). If desired, low frequency artifacts may be eliminated from the frequency domain signal by setting initial frequency bins (for example, a first five frequency bins) to a median magnitude level. The frequency domain spectrum may then be smoothed, without shifting, by convolving a rectangular window (for example, having window width of about 21.3% of a center frequency of the band). The convolved frequency domain signal may then be, optionally, reversed and convolved again, with or without the same rectangular window.

The center frequency is then estimated by identifying a peak of the smoothed and convolved magnitude spectrum.

If desired, the center frequency identified in Block 92 may be verified, for example, by time-shifting the associated, transmitted noise signal (Block 94). In that regard, the transmitted noise signal may be band-pass filtered into a one-third octave region, which is centered on an estimated peak frequency value. Input and output signal envelopes of the transmitted noise signal and the resultant acoustic signal, respectively, are estimated by squaring the respective waveforms and applying a low-pass filter (for example, having a frequency of 32 Hz).

The second and third data points, that is, coherence in time delays of the transmitted and resultant signals are identified according to Blocks 94 and 95, respectively. In that regard, a cross-correlation of the input and output signal envelopes may be calculated, and both a location and a magnitude of the cross-correlation function are identified. The cross-correlation function identified peak may be used to calculate (1) the desired coherence between the transmitted noise signal and the received acoustic signal and (2) the approximate time delay between the transmitted noise signal and the received acoustic signal. If coherence is insufficient (e.g., if coherence is less than about 0.5), then the estimated center frequency cannot be verified; otherwise, the approximate time delay may be presumed to be an estimate of a total time delay between the transmission of the noise signal from the speaker 24 (FIG. 2) and reception of the noise signal at the sound input device 27 (FIG. 2).

The fourth data point, that is, the output level of the transmitted noise signal, may be determined by a total energy in the one-third octave band centered about the estimated center frequency (Block 96).

Because the exemplary method illustrated in FIG. 1 includes both baseline and test hearing device configurations, each data point corresponding to the baseline data set may be compared to each data point corresponding to the test data sets. This comparison, according to one embodiment of the present invention, may be visually presented to facilitate a hearing professional's review of differences between the baseline and test configurations—that is, differences to use of the hearing aid 85 (FIG. 2).

Figure 7:
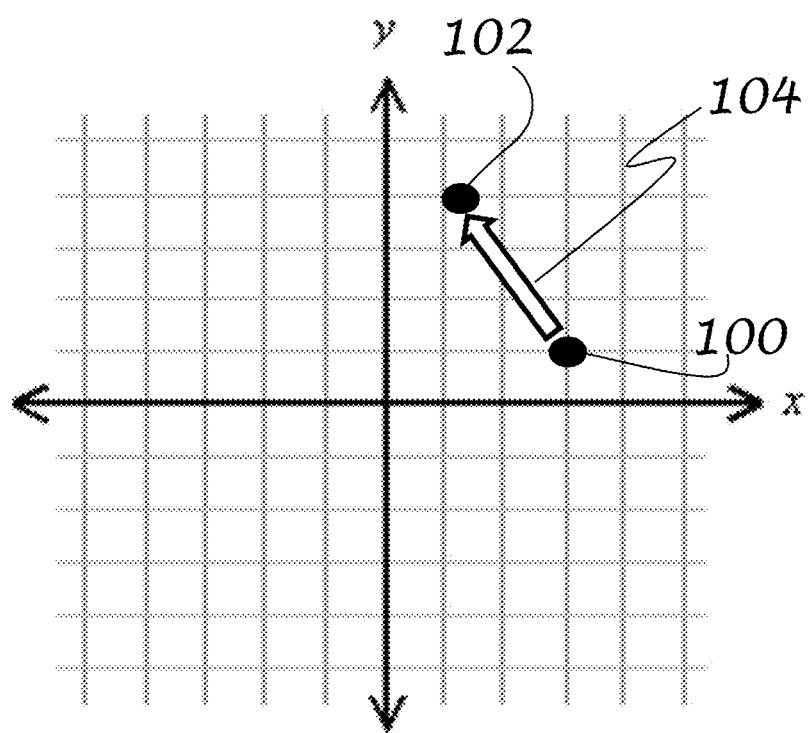
FIG. 7 is a graphical representation suitable for visualizing the analyzed data of FIG. 6, in accordance with an embodiment of the present invention.

FIG. 7 illustrates an exemplary method of visualizing differences between data points corresponding to the baseline and test data sets. Reference state data points 100 resulting from the baseline hearing device confirmation are compared to test state data points 102 resulting from the test hearing device configuration. As shown, the first data point (i.e., center frequency) may be plotted against the fourth data point (i.e., output level of transmitted noise signal). Once both the reference and test state data points are graphed, an arrow 104 may extend from the reference state data point 100 to the corresponding test state data point 102. If desired, additional data points may also be graphical displayed, for example, using multidimensional graphs incorporating a third axis, a color spectrum, an arrow thickness spectrum, or combinations thereof. It will be readily appreciated by the skilled artisan having the benefit of the disclosure herein that the data point values need not be limited to quadrant I, as shown, nor must a direction of the variation in the signal be as shown.

The resulting graph includes a plurality of reference state data points and a corresponding plurality of test state data points joined by a plurality of arrows 104. Such manner of visualization simultaneously and readily conveys shifts or changes in acoustical signal due to the hearing aid 85, which facilitates the hearing professional's attempt to adjust the hearing aid so as to fit the particular requirements of a patient. Such ability to visualize the hearing device performance further provides a significant advantage over conventional acoustic verification systems, the latter of which being capable of only displaying the effect of frequency lowering on a single input frequency at a time.

The arrow-based visualization method according to embodiments of the present invention may also provide benefit for those patients having a hearing device that does not shift the frequency of the output signal. The systematic cycling of frequency and level, as described with embodiments of the present invention, and the associated arrow-based visualization of differences in gain at different input levels, provides a more complete and intuitive analysis as compared with conventional systems.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

Figure 8A:
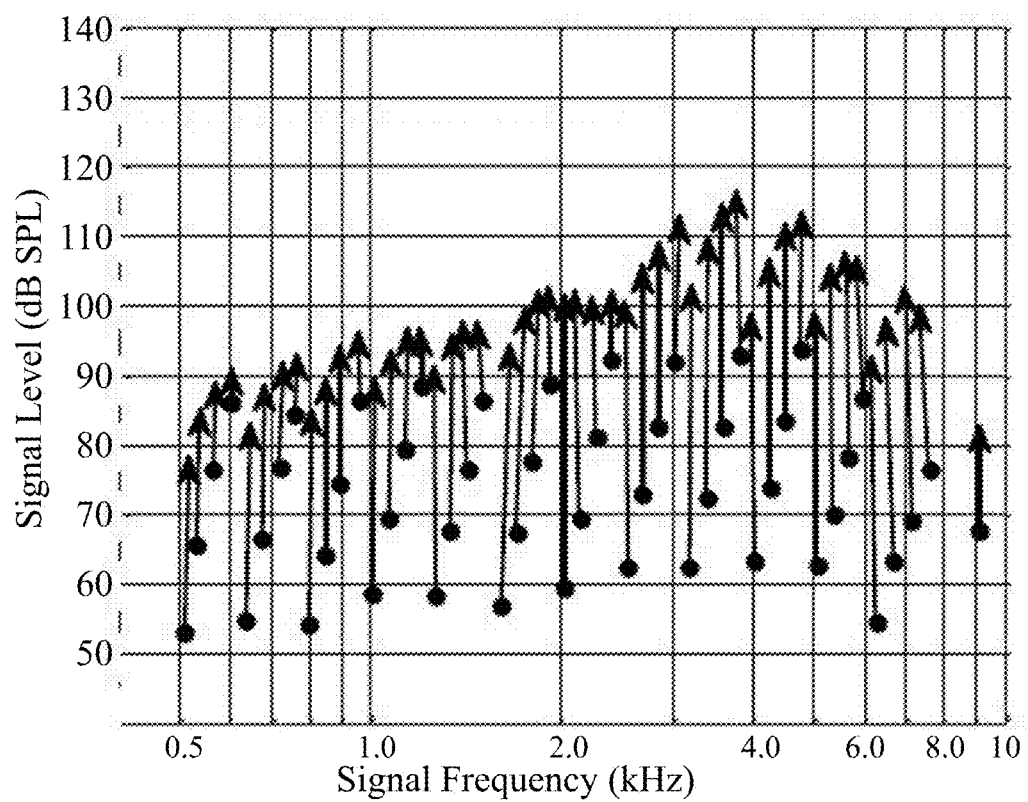
FIGS. 8A-8C are graphical visualizations of a first exemplary data acquired by the method illustrated in FIG. 1.
Figure 8B:
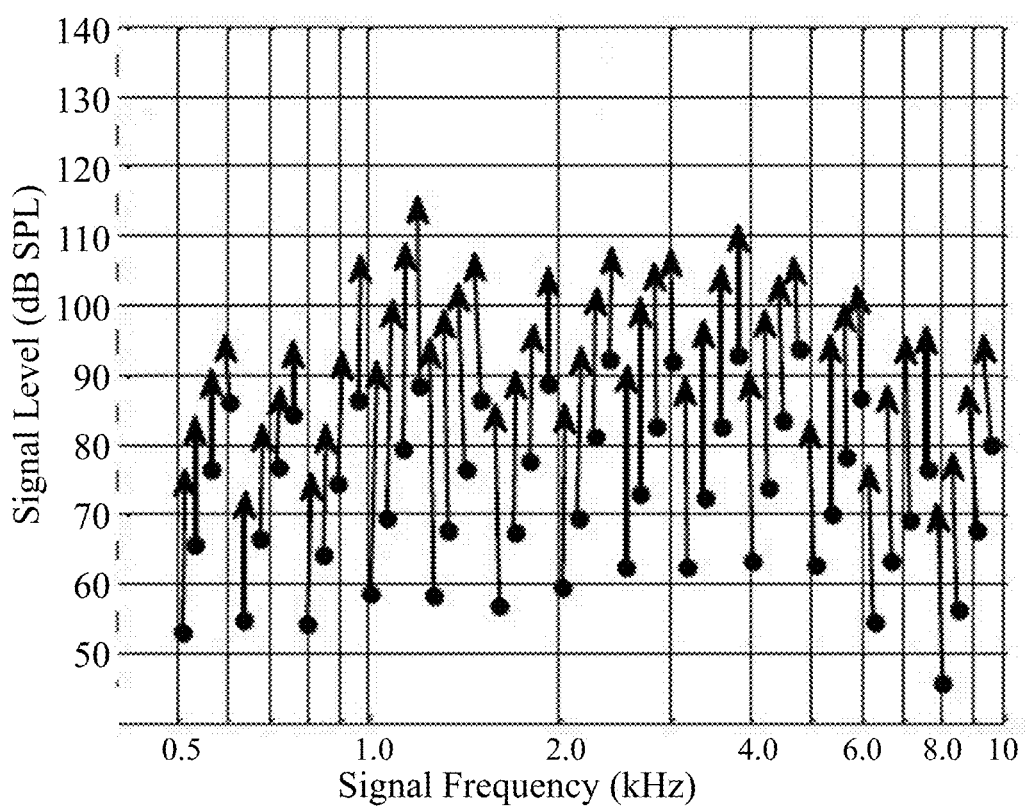
Figure 8C:
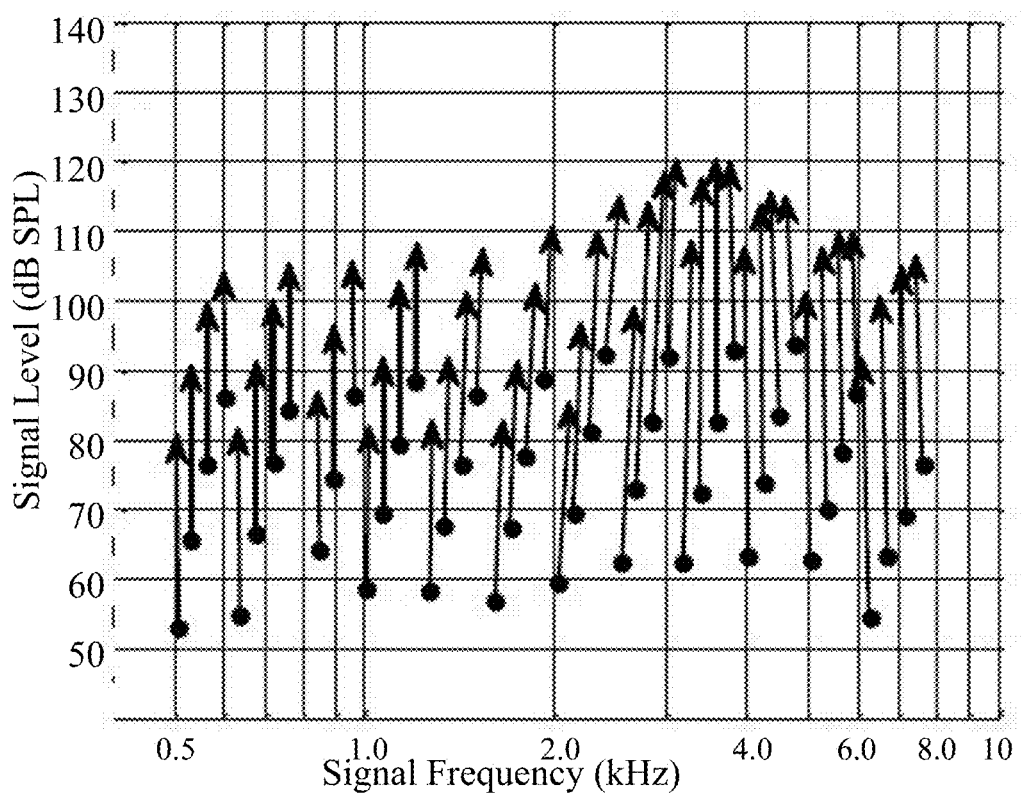

FIGS. 8A-8C are graphical representations of data points acquired according to embodiments of the present invention for three commercially-available hearing aid devices (Phonak, Widex, and Starkey, respectively), each equipped with a nonlinear frequency compression capability but operated in a mode wherein the frequency compression feature is disabled. The reference state was an unaided ear while the test state included the hearing device as described. Each data point (closed circle) represents frequency and level of signals measured in the reference state for each of 52 noise signal frequency bands tested. Each data point is connected by an arrow that terminates at the frequency and level of signals measured in the test state for the same noise signal frequency band. Only measurements considered to be valid for both the reference and test states were plotted.

Data points for some frequency bands are missing from the high frequency regions because the produced outputs fell below the noise floor in the test states. The resultant coherence values between the envelope of the input noise waveform and the envelope of the output noise waveform were below the threshold coherence value, which was set as a minimum acceptable level for a valid measurement.

The staggered pattern of the dots indicates SPL differences between successive ones of the noise signals. Staggering of SPL across frequencies facilitates visualization of the data points by reducing overlap of the data points and arrows.

As shown, lengths of the arrows decrease with higher output levels, which is indicative of the effects of dynamic compression in the hearing device. Said another way, the decrease in length corresponds to the hearing aids capability to amplify low-level sounds more than high-level sounds, within each frequency band.

Finally, each data point does not necessarily fall at 50 dB, 60 dB, 70 dB, and 80 dB. Such shifts represent acoustic transformations caused by the head and torso of the acoustic manikin. Such variations are known to those having ordinary skill in the art of head-related transfer functions.

Example 2

Figure 9A:
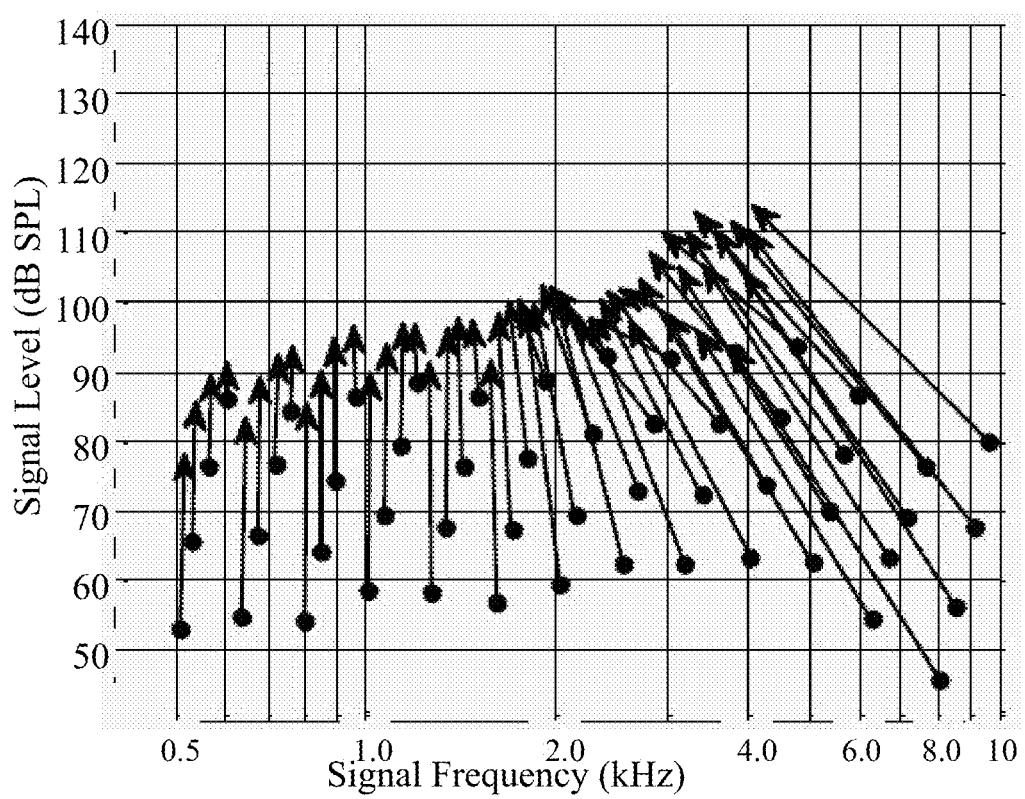
FIGS. 9A-9C are graphical visualizations of a second exemplary data acquired by the method illustrated in FIG. 1.
Figure 9B:
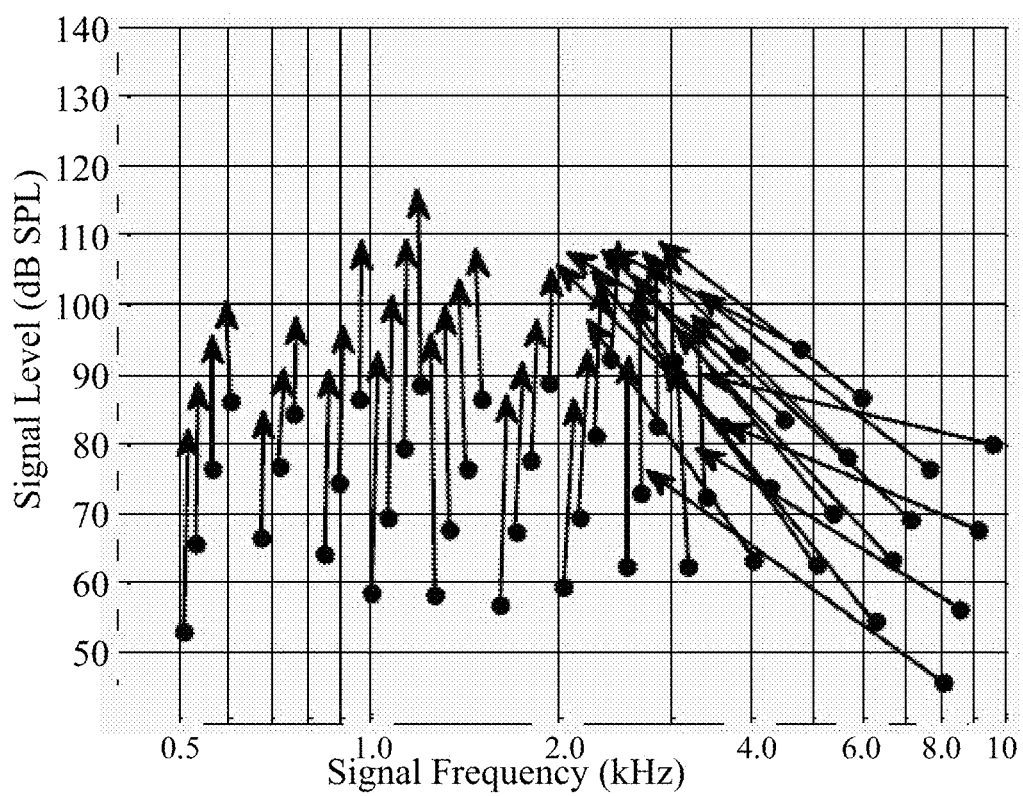
Figure 9C:
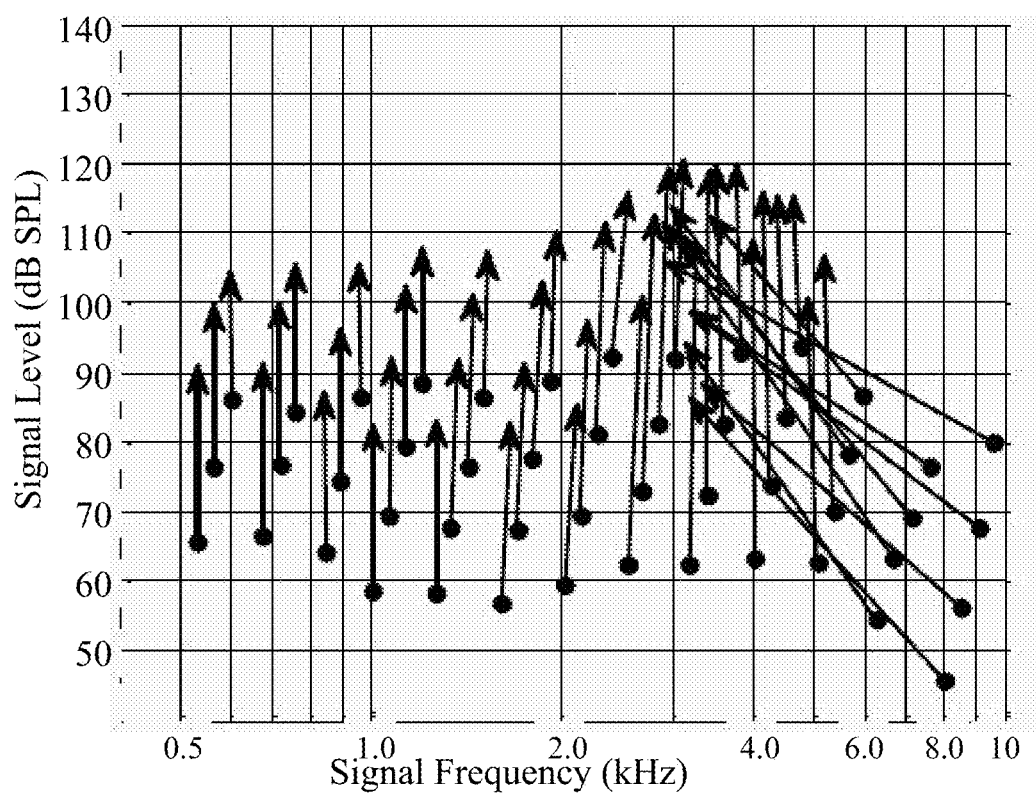

FIGS. 9A-9C are graphical representations of data points acquired according to embodiments of the present invention for the same three commercially-available hearing aid devices used in Example 1 but with the frequency compression feature enabled. The reference state was, again, an unaided ear while the test state included a hearing device with combined, conventional wide-band dynamic compression with a non-linear frequency compression algorithm. Each data point (closed circle) represents frequency and level measured in the reference state for each of 52 noise signal frequency bands tested. Each data point is connected by an arrow that terminates at the frequency and level of signals measured in the test state for the same noise signal frequency band. Only measurements considered to be valid for both the reference and test states were plotted.

As shown in FIGS. 9A-9C, arrows originating at low frequencies (below 2 kHz or 3 kHz) are approximately vertical and roughly match corresponding data of FIGS. 8A-8C. This correlation at low frequencies indicates that the frequency lowering algorithms in these hearing aids are only effective at frequencies above a particular cutoff frequency. The cutoff frequency varies according to the make and model of the device and the settings used to program the device. The frequency value at which direction of the arrows changes from a vertical orientation to a sloped orientation (as shown, arrows are sloping upwardly and toward the left) indicates a frequency at which the frequency lowering algorithm in each device becomes active.

In FIG. 9A, the hearing aid tested utilized a "frequency compression" algorithm, wherein each high frequency input value is shifted to a unique low frequency value.

In FIG. 9B, the hearing aid tested utilized a "frequency transposition" algorithm, which does not frequency shift low-frequency auditory signals but, rather, shifts high frequency audio signals into a lower, auditory range. High frequency audio signals are added to the existing low-frequency audio signal. This characteristic of the tested hearing aid is demonstrated by multiple arrows originating from different frequencies (within the reference state data points) but terminating at similar frequencies (within the test state data points).

In FIG. 9C, the hearing aid tested appears to use a combination of both frequency compression and frequency transposition. The visualization provided in FIG. 9C facilitates an analysis of the hearing aid over a wide range of input signals that parametrically vary both in frequency and amplitude, within a single plot.

Example 3

Figure 10:
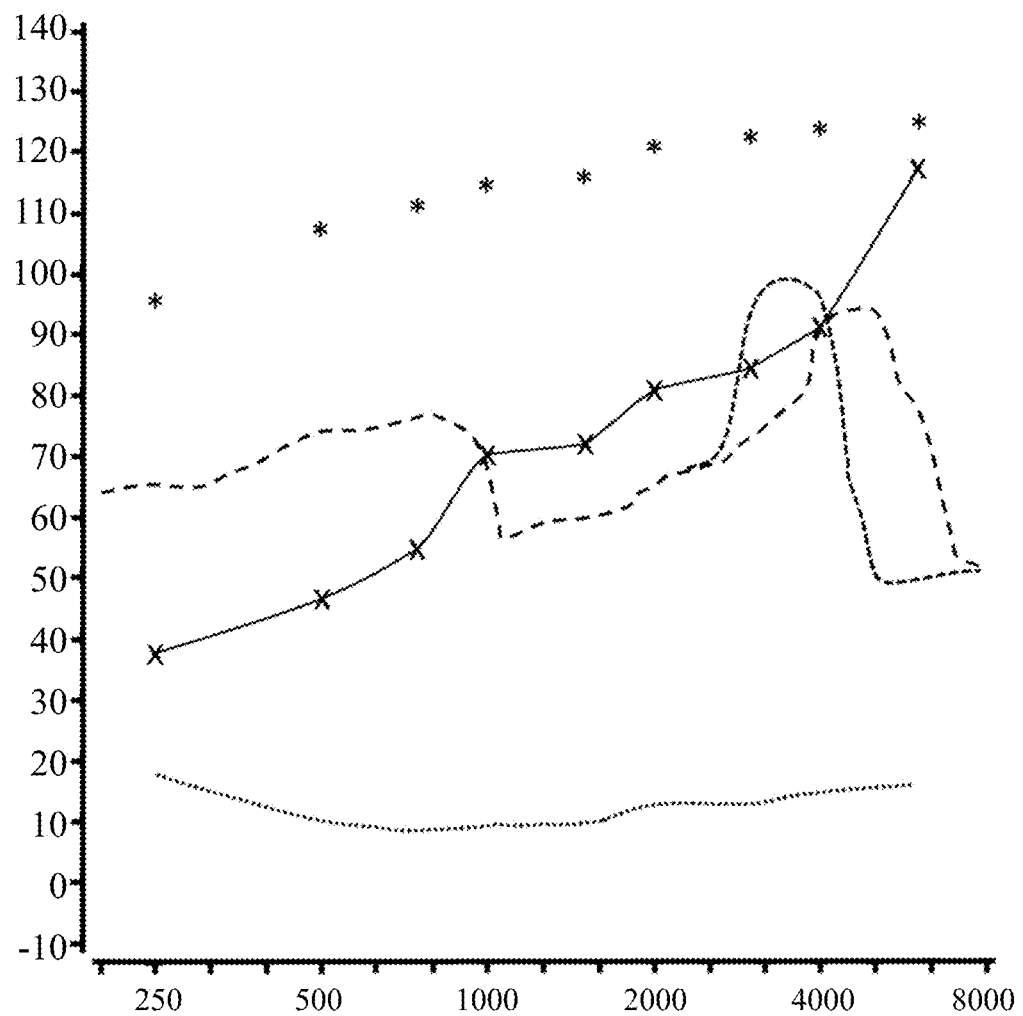
FIG. 10 is a graphical visualization of data acquired and analyzed in accordance with conventional methods.
Figure 11:
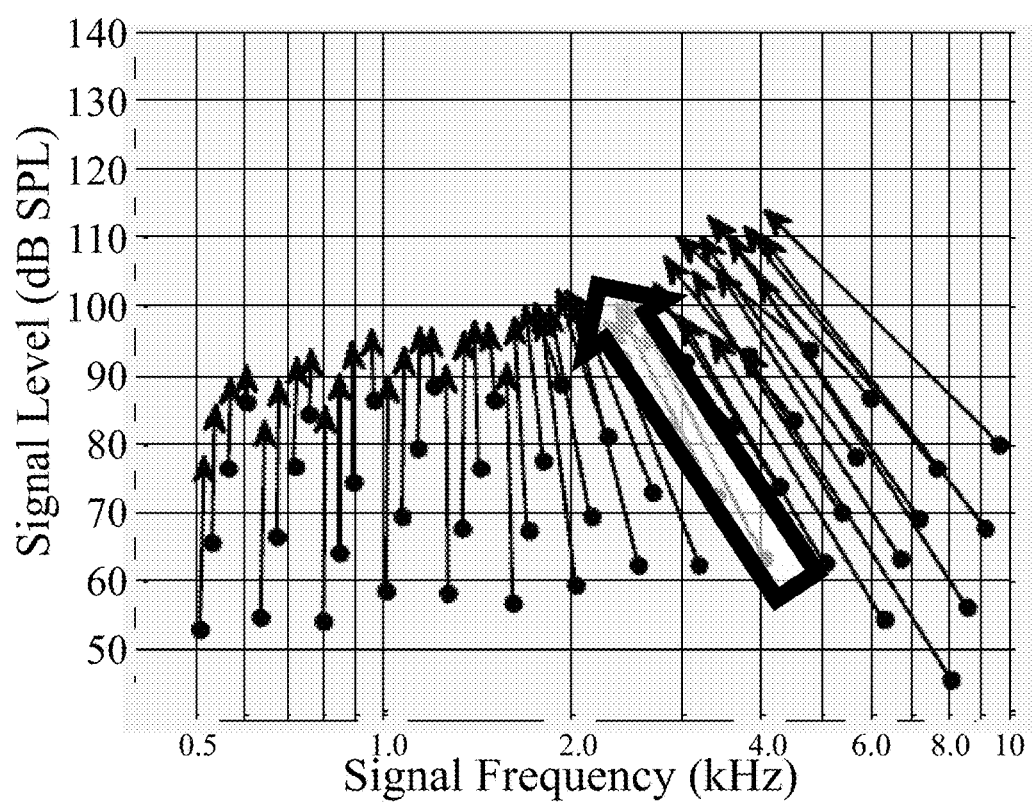
FIG. 11 is a graphical visualization of data, similar to the data of FIG. 10, but acquired and analyzed in accordance with an embodiment of the present invention.

FIGS. 10 and 11 are graphical representations of analysis of the same hearing aid (Speech 5000 having aided long-term-average speech spectrum) using the conventional, acoustic verification process for frequency lowering on a single input audio band and using visualization method described herein and according to an embodiment of the present invention, respectively.

FIG. 10 illustrates a deficiency of conventional acoustic verification systems for hearing aids, which was designed to evaluate gain characteristics of traditional hearing aids. These traditional hearing aids did not change the frequency composition of the output signal. Simple auditory systems that have level-dependent gain, without shifting the output frequency of the signal, can be easily displayed by producing a broadband input signal and measuring a broadband output signal. The magnitude frequency response of both signals may be displayed on the single graph using different colors. However, this procedure is poorly suited for evaluating frequency lowering hearing aids because, even if there is an apparent change in the bandwidth of the signal, there is no way to know which frequencies in the input signal were remapped to specific frequencies in the output signal. To evaluate frequency lowering hearing aids, manufacturers have adopted the relatively inefficient procedure of evaluating single ⅓rd octave bands of noise, one at a time.

As shown in FIG. 10, the long dashed line represents an output of the hearing aid with frequency lowering off. The short dashed line represents an output of the hearing aid with frequency lowering on. FIG. 10 only enables the audiologist to view one small component of the overall performance of the hearing aid at a time. Such dissociation of each component makes diagnosis and/or hearing aid adjustments difficult because, for example any change in the hearing aid settings to fix a gain problem in one band may likely result in unintended consequences in another portion of the frequency spectrum.

With specific reference now to FIG. 11, the graphical visualization displays all data acquired, which can be further reduced to a single arrow on the display. Presenting all information in a single screen can provide intuitions and insights about the performance of the hearing aid that would be almost impossible to obtain from the graphical representation of FIG. 10 or other conventional systems only displaying one frequency and one amplitude at a time. For example, it would be very difficult to use the conventional display to differentiate between the "frequency compression" and "frequency transposition" algorithms used by the hearing aids tested in FIGS. 8A and 8B.

As is described in detail herein, a method and apparatus for analyzing and visualizing the performance of frequency lowering hearing aids provides particular benefits over conventional methods and apparatii.

The addition of a metric evaluation of cross-correlation and coherence between the input test signal and the output signal of the disclosed method provides yet two additional benefits over conventional acoustic verification systems. Firstly, the coherence between envelopes provides insight as to a level of distortion generated by the hearing aid devices as part of the frequency lowering algorithm. In conventional hearing aid verification systems, only magnitude spectra of the input and output signals are measured, which provide no information as to whether the relevant speech information (known to be carried by low-frequency (4-16 Hz) modulations in the envelope of the speech signal) has been faithfully preserved during the frequency shifting process. By evaluating the coherence between the input signal and the frequency-shifted output signal, methods and systems according to embodiments of the present invention provide a way of ensuring frequency shifted signal is, in-fact, a frequency shifted version of the input and not a random noise signal having similar bandwidth at a lower frequency. No conventional verification system has this capability and, in-fact, many of the distortion evaluation measures implemented by these conventional hearing aid verification systems would consider any frequency range shift to be a distortion. As a result, it is difficult to measure the signal fidelity and distortion of frequency lowering hearing aids with conventional acoustic validation procedures.

Secondly, cross-correlation provides the benefit of access to information about the processing delay occurring within individual frequency bands of the hearing aid system. This information, which could be presented by adding a color code to the arrows in the plot (as was noted above) and makes it possible to determine whether the hearing aid processing algorithms is delaying some frequency bands more than others. Such processing delays may lead to problems in speech intelligibility. Cross-correlation also provides a convenient way of determining those portions of the output represent signals that have been processed by the hearing aid (and thus would have a significant measurable processing delay) and those portions representing acoustic leakage of the source input directly into the ear canal (which would have no processing delay).

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of analyzing performance of a frequency lowering hearing aid, the method comprising:
generating a sequence of successive noise signals, wherein the sequence of successive noise signals comprises a plurality of one-third octave band noise signals, and wherein the sequence of successive noise signals covers a range of frequencies;
transmitting acoustical sounds from a sound output device in response to the sequence of noise signals;
recording the acoustical sounds with a sound input device and saving as a first device data;
recording the acoustical sounds with the sound input device and a frequency lowering hearing aid and saving as a second device data; and
comparing the second device data to the first device data using an arrow-based visualization method comprising generating a single graphical display of changes in center frequencies and output levels of the transmitted noise signal of the first device data and the second device data comprising plotting values of the center frequencies and the output levels of the transmitted noise signal of the first device data, and extending an arrow from the plotted values of the center frequencies and the output levels of the transmitted noise signal of the first device data to values of the center frequencies and the output levels of the transmitted noise signal of the corresponding second device data.

2. The method of claim 1, further comprising modulating the plurality of one-third octave band noise signals with an envelope having random variations within a speech perception frequencies.

3. The method of claim 2 wherein said random variations within speech perception frequencies range from about 4 Hz to about 16 Hz.

4. The method of claim 1, further comprising:
calibrating at least one of the sound output device, the sound input device, and the frequency lowering hearing aid.

5. The method of claim 1, wherein the center frequency for each of the first and second device data is identified by:
windowing each of the first and second device data;
transforming each of the windowed first and second device data to respective first and second frequency data;
smoothing the first and second frequency data; and
finding a maximum within the smoothed first and second frequency data.

6. The method of claim 5, wherein the windowing includes applying a Hanning window.

7. The method of claim 5, wherein the smoothing of the frequency domain includes convolving a rectangular window.

8. The method of claim 1, further comprising:
verifying a validity of each of said identified center frequency of the first and second device data.

9. The method of claim 8, wherein said verifying of the validity of each of said identified center frequencies comprises
estimating the envelope of the recorded acoustical sounds of the first device data by squaring the waveform of said recorded acoustical sounds of the first device data and applying a low-pass filter having a frequency of 32 Hz;
estimating the envelope of the recorded acoustical sounds of the second device data by squaring the waveform of said recorded acoustical sounds of the second device data and applying a low-pass filter having a frequency of 32 Hz; and
determining coherence between the envelope of the recorded acoustical sounds of the first device data and the envelope of the recorded acoustical sounds of the second device data.

10. The method of claim 9, the method further comprising removing the recorded acoustical sounds of the first and second device data when the coherence between the envelope of the recorded acoustical sounds of the first device data and the envelope of the recorded acoustical sounds of the second device data is less than about 0.5.

11. The method of claim 1, wherein a change in a color, a thickness, or both, of the arrows may be used to graphically visualize changes in the first device data, the second device data, or both.

12. The method of claim 1 wherein successive noise signal bands within each frequency octave of the sequence of successive noise signals are parametrically varied in amplitude.

13. The method of claim 12 wherein the parametric variation in amplitude is achieved by offsetting the sequence of successive noise signals with increasing sound pressure levels (SPLs).

14. The method of claim 13 wherein said increasing SPLs comprises a first SPL, a second SPL, a third SPL and a fourth SPL, wherein said first SPL is 50 dB, the second SPL is 60 dB, the third SPL is 70 dB and the fourth SPL is 80 dB.

15. The method of claim 1 wherein each said successive noise signal of the sequence is one twelfth octave higher in frequency than the immediately prior noise signal of the sequence.

16. The method of claim 1 wherein each successive noise signal of the sequence is one twelfth octave higher in frequency than the immediately prior noise signal of the sequence, and the output level is set to 50 dB for a first 1/12th octave of each 1/3rd octave band, 60 dB for a second 1/12th octave of each 1/3rd octave band, 70 dB for a third 1/12th octave of each 1/3rd octave band, and 80 dB for a fourth 1/12th octave of each 1/3rd octave band.

17. The method of claim 1 wherein the range of frequencies is from about 500 Hz to about 9514 Hz.

* * * * *